(12) United States Patent
Chapleo et al.

(10) Patent No.: US 6,995,169 B2
(45) Date of Patent: Feb. 7, 2006

(54) ANALGESIC COMPOSITIONS CONTAINING BUPRENORPHINE

(75) Inventors: Christopher Bourne Chapleo, Gainsborough (GB); Nicolas Calvert Varey, Goole (GB); Keith McCormack, Kilburn (GB)

(73) Assignee: Reckitt Benckiser Healthcare (UK) Limited, Slough (GB)

( * ) Notice: Subject to any disclaimer, the term of this patent is extended or adjusted under 35 U.S.C. 154(b) by 13 days.

(21) Appl. No.: 10/145,284

(22) Filed: May 14, 2002

(65) Prior Publication Data

US 2003/0004178 A1 Jan. 2, 2003

Related U.S. Application Data

(63) Continuation-in-part of application No. PCT/GB00/04372, filed on Nov. 17, 2000.

(60) Provisional application No. 60/176,208, filed on Jan. 14, 2000.

(30) Foreign Application Priority Data

Nov. 19, 1999 (GB) .................................... 9927359

(51) Int. Cl.
*A61K 31/44* (2006.01)
(52) U.S. Cl. ........................ 514/282; 514/811; 514/812
(58) Field of Classification Search ................ 514/282, 514/811, 812
See application file for complete search history.

(56) References Cited

U.S. PATENT DOCUMENTS 5,512,578 A * 4/1996 Crain et al. .................. 514/282

FOREIGN PATENT DOCUMENTS

| GB | 2 150 832 A | | 7/1985 |
| GB | 2 167 832 A | | 6/1986 |
| GB | 2167663 A | * | 6/1986 |
| WO | WO 96/02251 | | 2/1996 |

OTHER PUBLICATIONS

XP-001010201, Thomas Eissenberg et al., "Buprenorphine's Physical Dependence Potential: Antagonist-Precepitated Withdrawal in Humans 1", The Journal of Pharmacology and Experimental Therapeutics, The American Society for Pharmacology and Experimental Therapeutics, JPET vol. 276: pp. 449-459, 1996.

* cited by examiner

*Primary Examiner*—Sreeni Padmanabhan
*Assistant Examiner*—Jennifer Kim
(74) *Attorney, Agent, or Firm*—Fish & Richardson P.C.

(57) ABSTRACT

An analgesic composition in parenteral unit dosage form or in a unit dosage form suitable for delivery via the mucosa comprising an amount of buprenorphine which is less than the clinical dose required to achieve pain relief and an amount of naloxone such that the ratio by weight of buprenorphine to naloxone is in the range of from 12.5:1 to 27.5:1, or an amount of naltrexone or nalmefene such that the ratio by weight of buprenorphine to naltrexone or nalmefene is in the range of from 12.5:1 to 22.5:1. The analgesic action of the buprenorphine is potentiated by the low dose of naloxone, naltrexone or nalmefene.

5 Claims, 3 Drawing Sheets ions Containing
ANALGESIC COMPOSITIONS CONTAINING BUPRENORPHINE

CROSS REFERENCE TO RELATED APPLICATION

This is a continuation-in-part of application No. PCT/GB00/04372 filed on 17 Nov. 2000, which claims the benefit of U.S. Provisional Application No. 60/176,208 filed on 14 Jan. 2000.

FIELD OF THE INVENTION

The present invention relates to analgesic compositions, containing buprenorphine and, in particular, to compositions which contain buprenorphine at a sub-clinical analgesic dose level in combination with naloxone, naltrexone or nalmefene.

BACKGROUND OF THE INVENTION

Buprenorphine (International Non-proprietary Name for N-cyclopropylmethyl-7α-[1-(S)-hydroxy-1,2,2-trimethyl-propyl]6,14-endoethano-6,7,8,14-tetrahydro-nororipavine) has been shown in clinical trials to be a potent opiate partial agonist analgesic lacking the psychotomimetic effects found with other opiate analgesics. Buprenorphine effectively relieves moderate to severe pain in doses of 0.1 mg or more administered either parenterally or sublingually. The optimum therapeutic range for single doses is 0.3 mg–0.6 mg by injection and 0.2 mg–0.8 mg for sublingual tablets.

In animal tests and in man buprenorphine has been shown to have both agonist (morphine-like) and antagonist properties. However from direct dependence studies in animals and in man it has been concluded that buprenorphine does not produce significant physical dependence, as indicated by animal self administration studies and by the measurement of euphorigenic effects in human post addicts. However, buprenorphine suffers from side effects typical of opiate agonists such as nausea and vomiting, constipation and respiratory depression in some patients, although there is a ceiling to its effects on respiratory depression as a direct consequence of its partial agonist properties.

Naloxone (International Non-proprietary Name for 1-N-allyl-14-hydroxynorhydromorphinone) is a narcotic antagonist which has been incorporated into oral and sublingual preparations of various opioids in order to protect the preparations from parenteral abuse, whilst maintaining the analgesic effect of the opioid.

GB-A-2150832 describes analgesic compositions in sublingual or parenteral dosage form comprising an active dose of buprenorphine and an amount of naloxone sufficient to prove aversive to a narcotic addict by parenteral administration but insufficient to compromise the analgesic action of the buprenorphine. Preferably the parenteral dosage form contains naloxone and buprenorphine within the weight ratio of 1:3 to 1:1 and the sublingual form within the ratio 1:2 to 2:1.

Naltrexone (International Non-proprietary Name for 1-N-cyclopropylmethyl-14-hydroxynordihydro-morphinone) is a pure opiate antagonist which, when administered orally (50 mg/day) as a maintenance drug for opiate addicts, blocks the effects of self-administered opiates and this contributes to the extinction of drug craving.

Nalmefene (International Non-Proprietary Name for (5)-17-(cyclopropylmethyl)-4,5-epoxy-6-methylene-morphinan-3,14-diol) is a structural analogue of naltrexone with opiate antagonist activity.

GB-A-2167633 describes an analgesic composition in parenteral or sublingual unit dosage form comprising an active dose of buprenorphine and an amount of naltrexone sufficient to prove aversive to a narcotic addict by parenteral administration but insufficient to compromise the analgesic action of the buprenorphine wherein the dose of buprenorphine in the parenteral form is from about 0.3 mg to about 0.6 mg and in the sublingual form from about 0.1 mg to about 0.4 mg and the weights of buprenorphine to naltrexone for the parenteral form are within the ratio of 12:1 to 3:1 and for the sublingual form are within the ratio 4:1 to 1:1.

SUMMARY OF THE INVENTION

We have now surprisingly found that sub-clinical dosage levels of buprenorphine are potentiated and enhanced by low doses of naloxone or naltrexone or nalmefene. The interaction between the drugs is a synergistic interaction and more than the additive effects of the separate drug entities.

DETAILED DISCLOSURE

Figure 1:
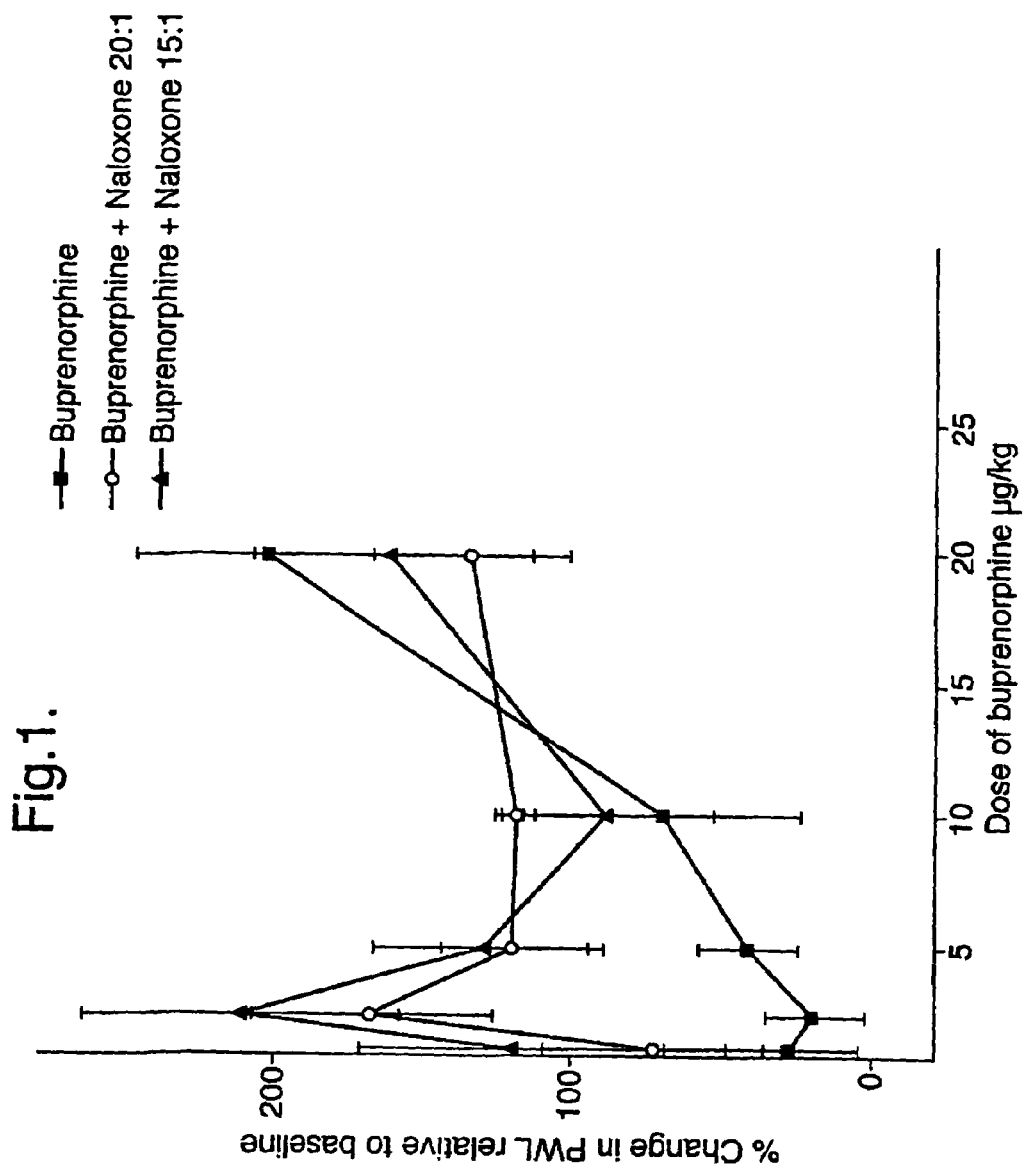
FIG. 1 is graph showing the results of the tests done according to Example 1.

Accordingly, the present invention provides in its broadest aspect an analgesic composition in parenteral unit dosage form or in a unit dosage form suitable for delivery via the mucosa comprising an amount of buprenorphine which is less than the clinical dose required to achieve pain relief and
  (i) an amount of naloxone such that the ratio by weight of buprenorphine to naloxone is in the range of from 12.5:1 to 27.5:1, or
  (ii) an amount of naltrexone or nalmefene such that the ratio by weight of buprenorphine to naltrexone or nalmefene is in the range of from 12.5:1 to 22.5:1 whereby the analgesic action of the buprenorphine is potentiated by the low dose of naloxone, naltrexone or nalmefene.

In a first aspect the present invention provides an analgesic composition in parenteral or sublingual unit dosage form or in a unit dosage form suitable for delivery via the mucosa comprising from 15 μg to 200 μg of buprenorphine per unit dose and
  (i) an amount of naloxone such that the ratio by weight of buprenorphine to naloxone is in the range of from 12.5:1 to 27.5:1, or
  (ii) an amount of naltrexone or nalmefene such that the ratio by weight of buprenorphine to naltrexone or nalmefene is in the range of from 12.5:1 to 22.5:1.

It is to be understood that the terms buprenorphine, naloxone, naltrexone and nalmefene as used herein are meant to cover not only the bases but their pharmaceutically acceptable salts. Particularly preferred salts are the hydrochlorides.

It is preferable to formulate the compositions in unit dosage forms i.e. physically discrete units containing the appropriate amounts of buprenorphine and naloxone, naltrexone or nalmefene, together with pharmaceutically acceptable diluents and/or carriers. Such unit dosage forms for parenteral administration are suitably in the form of ampoules and for delivery via the mucosa may for example be in the form of tablets for sublingual administration.

The term parenteral is intended to encompass administration of the compositions by any way other than through the alimentary tract.

The term mucosa is intended to encompass any mucous membrane and includes oral mucosa, rectal mucosa, vaginal mucosa and nasal mucosa.

Compositions intended for parenteral administration comprise an isotonic solution of buprenorphine and naloxone, naltrexone or nalmefene in sterile water. Conveniently the solution is made isotonic by use of dextrose and sterilised by autoclaving or by filtration through a membrane filter. The compositions may be administered intramuscularly, intradermally, intraperitonealy, intravenously, intraarterially, subcutaneously or by the epidural route.

Compositions in the form of sublingual tablets contain soluble excipients such as lactose, mannitol, dextrose, sucrose or mixtures thereof. They will also contain granulating and disintegrating agents such as starch, binding agents such as povidone or hydroxypropyl-methyl cellulose and lubricating agents such as magnesium stearate.

The compositions for parenteral administration, or for delivery via the mucosa, such as by sublingual administration, as detailed above, may be prepared by manufacturing techniques which are well known to those skilled in the art.

The compositions of the present invention in unit dosage form preferably contain the naloxone, naltrexone or nalmefene in an amount such that the ratio by weight of buprenorphine to naloxone, naltrexone or nalmefene is in the range of from 15:1 to 20:1.

The compositions of the present invention contain buprenorphine in an amount which is below that required in a unit dose to obtain pain relief. In the human being, dosages of about 40 µg of buprenorphine per kilogram of body weight are required to obtain satisfactory pain relief in the absence of potentiation. Thus for typical body weights of 50 to 80 kg, the dosage would be from 2000 µg to 3200 µg, i.e. from 2 mg to 3.2 mg of buprenorphine per day. This would conveniently be administered as 4 unit doses. The amounts of buprenorphine which are effective in the present invention are below the amounts which are effective in the absence of the potentiating effects of naloxone, naltrexone or nalmefene.

In a second aspect the present invention provides a method for the treatment of pain in a human or animal subject, which method comprises the administration to the human or animal by the parenteral or via the mucosa route of from 1.25 µg to 10 µg per kilogram of body weight of buprenorphine per day and
(i) an amount of naloxone such that the ratio by weight of buprenorphine to naloxone administered is in the range of from 12.5:1 to 27.5:1, or
(ii) an amount of naltrexone or nalmefene such that the ratio by weight of buprenorphine to naltrexone or nalmefene administered is in the range of from 12.5:1 to 22.5:1.

In a third aspect the present invention provides the use of naloxone, naltrexone or nalmefene in the manufacture of a medicament for the treatment of pain comprising a sub-clinical amount of buprenorphine, wherein the ratio by weight of buprenorphine to naloxone is in the range of from 12.5:1 to 27.5:1 or the ratio by weight of buprenorphine to naltrexone or nalmefene is in the range of from 12.5:1 to 22.5:1.

The ratios for the potentiation of the sub-clinical dosages of buprenorphine by low doses of the opiate antagonists were determined by the University Department of Anaesthesia, Addenbrookes Hospital, Cambridge according to the paw withdrawal method of Hargreaves, K. M., Dubner, R., Brown, F., Flores, C. and Joris, J.: A New and Sensitive Method for Measuring Thermal Nociception in Cutaneous Hyperalgesia. *Pain* 32: 77–88, 1988. This method enables the researcher to discern a peripherally mediated response to thermal stimulation caused by drugs in the unrestrained rat.

The results were obtained using a BASILE Plantar Test Device (Ugo Basile, Comero, Italy). It basically consists of a movable I.R. (infrared) generator placed below a glass pane upon which the operator places the rat. A Perspex enclosure defines the space within which the animal is unrestrained. It is divided into three compartments, which helps the operator to carry out rapid "screening" work: up to three rats can be tested with no appreciable delay inbetween.

The operator positions the I.R. Generator directly beneath the hind paw of the rat and activates both the I.R. Source and a reaction time counter. When the rat feels pain and withdraws its paw, the I.R. Generator is automatically switched off and the timer stops, determining the withdrawal latency.

The effects of buprenorphine at various dosages, naloxone at various dosages, naltrexone at various dosages and buprenorphine in combination with naloxone or naltrexone at various dosages were determined by testing adult rats in which peripheral mononeuropathy was produced by placing three loosely constrictive ligatures around the common sciatic nerve. The testing was carried out on the eighth day following the operative procedure.

In order to determine a baseline for comparison purposes, rats were subjected to the Hargreaves paw withdrawal test before the subcutaneous injection of the various drugs or drug combinations being tested. The rats were then injected subcutaneously with the particular drug or drug combination being tested and the percentage change in time for the rat to withdraw its paw from the thermal stimulation, in comparison with the baseline, was recorded as a percentage in paw withdrawal latency.

The invention is further described with reference to the following Examples.

Methods

Surgery

Lister Hooded rats (180–200 g) were anaesthetised with halothane and the left sciatic nerve was loosely ligated with 3 chromic cat gut sutures to induce a neuropathy.

Rats were left to recover for one week after the procedure before commencing behavioural testing.

Drug Preparation

The drugs (buprenorphine, naloxone and naltrexone) were prepared freshly in water at a concentration of 1 mg/ml. The stocks were then diluted in saline to obtain the different concentrations used in the study.

Drugs were injected sub-cutaneously in the fold of the neck.

Testing

After 8 days, thermal nociceptive threshold, as determined by hindpaw withdrawal latency, was measured using a plantar test (Ugo Basile, Comero, Italy). Prior to testing, the rat was placed in the Perspex box and allowed 5 minutes to habituate. The heat source was positioned under the plantar surface of one hind paw at random and activated. This initiated a timing circuit which measured the time interval between the application of the light beam and the withdrawal of the hind paw. This value was assigned as the withdrawal latency.

Paw withdrawal latency was determined before injection and at different times after injection. Three measurements were taken per paw.

EXAMPLE 1

The effects of buprenorphine and buprenorphine/naloxone at weight ratios of 20:1 and 15:1 were determined at various doses of buprenorphine expressed as µg/kg of body weight of the drug administered subcutaneously to rats (n=3).

The results of these tests are given in FIG. 1. The potentiation of sub-clinical doses of buprenorphine by low dose naloxone can be clearly seen from the graph of FIG. 1. Both of the buprenorphine/naloxone combinations showed marked increases in pain withdrawal latencies at both weight ratios where the buprenorphine dose was 1.25 µg and 2.5 µg, compared to buprenorphine alone which had no significant effect at these dosage levels.

EXAMPLE 2

Buprenorphine was administered to rats (n=6) at a dosage level of 2.5 µg/kg of body weight of the rats. Buprenorphine was co-administered subcutaneously with either naloxone or naltrexone at various weight ratios ranging from 5:1 to 30:1. In order to provide appropriate baseline points naloxone and naltrexone alone were also administered subcutaneously to rats at the same dosage levels as those used in the combined treatments.

Figure 2:
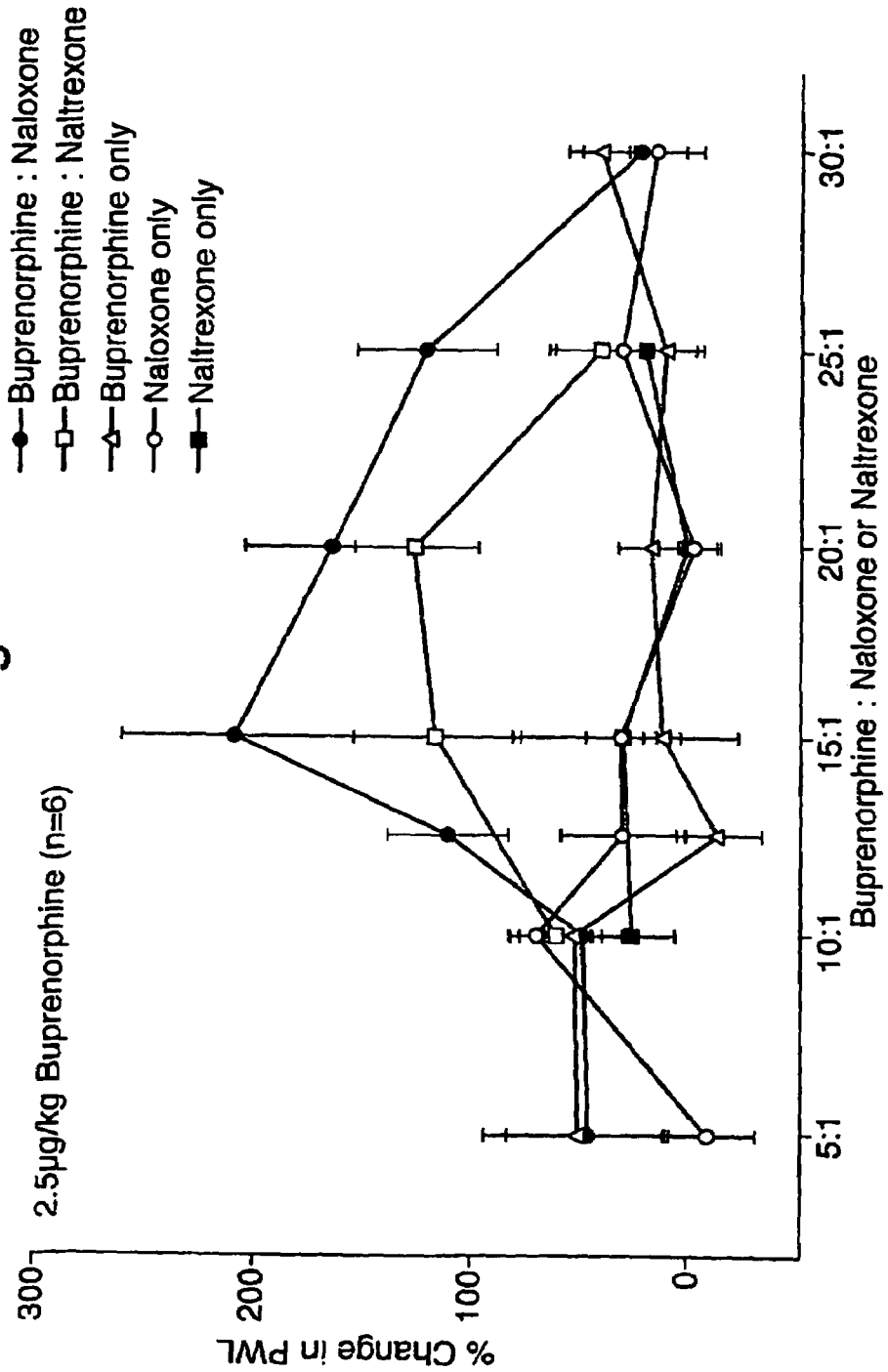
FIG. 2 is a graph showing the results of the tests done according to Example 2.

The results are given in FIG. 2 from which the potentiation of the sub-clinical doses of buprenorphine by naloxone or naltrexone can be clearly seen.

EXAMPLE 3

Figure 3:
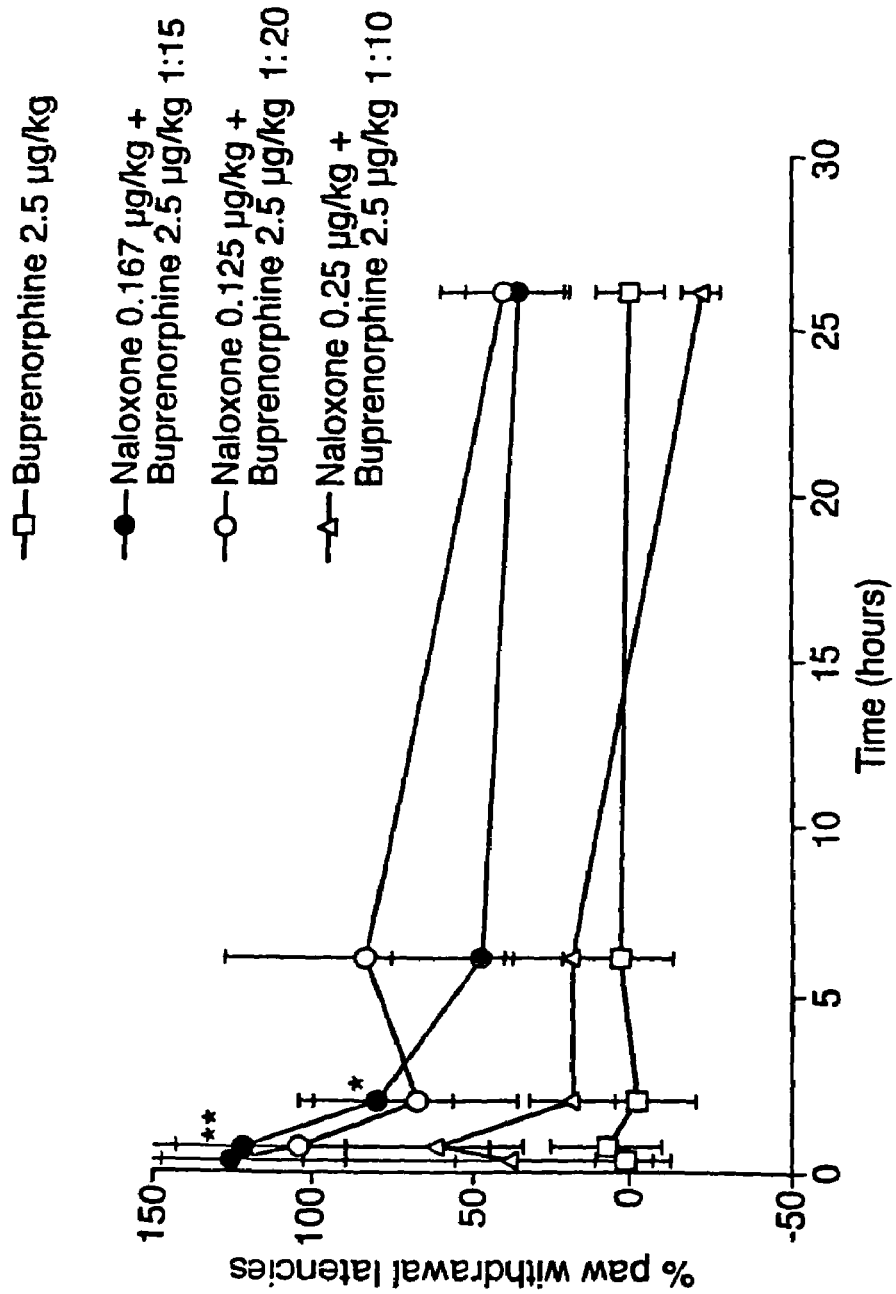
FIG. 3 is a graph showing the results of the tests done according to Example 3.

To investigate the duration of action of several ratios (10:1, 15:1 and 20:1 buprenorphine:naloxone, with a fixed dose of buprenorphine) the effect on PWL was followed over a 26 hour period following subcutaneous injection. The results are given in FIG. 3 from which it can be seen that the effect was already maximal after 40 minutes and then decreased sharply over 6 hours. However at 26 hours a residual effect was still visible, although this was not statistically significant. The maximal effect of each ratio (40 min) was compatible with the results shown in FIG. 2. The effect observed with the 10:1 ratio combination was not statistically significant.

EXAMPLE 4

A parenteral formulation having the following composition:

|  | mg/ml. |
| --- | --- |
| Buprenorphine HCl | 0.1 |
| Naloxone HCl | 0.0067 |
| Anhydrous dextrose | 50.0 |
| Hydrochloric acid to pH | 4.0 |
| Water for injection to | 1.0 ml | was prepared by dissolving dextrose, buprenorphine hydrochloride and naloxone hydrochloride in that order with stirring, in about 95% batch volume of Water for Injection. The acidity of the solution was adjusted to pH 4.0 by the addition of 0.1M hydrochloric acid, and the solution was made up to volume with Water for Injection. The solution was filtered through a 0.22 µm membrane filter and transferred to sterilised 1 ml or 2 ml glass ampoules containing 1 ml or 2 ml of the solution. The ampoules were sealed and the product sterilised by autoclaving.

EXAMPLE 5

The formulation of Example 4 was varied by using 0.005 mg/ml of naloxone hydrochloride instead of 0.0667 mg/ml.

EXAMPLE 6

The formulation of Example 4 was modified with 0.0067 mg/ml of naltrexone hydrochloride substituted for the naloxone hydrochloride of Example 1.

EXAMPLE 7

The formulation of Example 4 was modified with 0.005 mg/ml of naltrexone hydrochloride substituted for the naloxone hydrochloride of Example 1.

EXAMPLE 8

The formulation of Example 4 was modified with 0.0067 mg/ml of nalmefene hydrochloride substituted for the naloxone hydrochloride of Example 4.

EXAMPLE 9

The formulation of Example 4 was modified with 0.0005 mg/ml of nalmefene hydrochloride substituted for the naloxone hydrochloride of Example 4.

EXAMPLE 10

A sublingual tablet having the following composition:

|  | mg/tablet |
| --- | --- |
| Buprenorphine HCl | 0.1 |
| Naloxone HCl | 0.0067 |
| Lactose | 31.2433 |
| Mannitol | 18.0 |
| Maize starch | 9.0 |
| Povidone | 1.2 |
| Magnesium stearate | 0.45 |
|  | 60.0 | was prepared by screening all the materials with the exception of the magnesium stearate through a 750 µm sieve and blending them together. The mixed powders were then subjected to an aqueous granulation procedure and dried at 50° C. The resulting granules were forced through a 750 µm sieve and blended with magnesium stearate (pre-sieved through a 500 µm sieve). The tablet granules were compressed to yield tablets of 5.56 mm diameter and weight 60 mg.

EXAMPLE 11

The formulation of Example 10 was varied by using 0.005 mg/tablet of naloxone hydrochloride and adjusting the weight of lactose.

EXAMPLE 12

The formulation of Example 10 was modified with 0.0067 mg/tablet of naltrexone hydrochloride substituted for the naloxone hydrochloride of Example 10.

EXAMPLE 13

The formulation of Example 10 was modified with 0.005 mg/tablet of naltrexone hydrochloride substituted for the naloxone hydrochloride of Example 10.

EXAMPLE 14

The formulation of Example 10 was modified with 0.0067 mg/tablet of nalmefene hydrochloride substituted for the naloxone hydrochloride of Example 10.

EXAMPLE 15

The formulation of Example 10 was modified with 0.005 mg/tablet of nalmefene hydrochloride substituted for the naloxone hydrochloride of Example 10.

EXAMPLE 16

A suppository having the following composition:

|  | mg/suppository |
| --- | --- |
| Buprenorphine HCl | 0.1 |
| Naloxone HCl | 0.0067 |
| Gelatin | 200 |
| Glycerin | 700 |
| Deionised water | 89.9 | was prepared by mixing the ingredients together and melting them at between 60° C. and 70° C. The melted mass is poured into a disposable mould of plastic material in which the suppositories are cast and remain enclosed until removed by the patient.

EXAMPLE 17

The formulation of Example 16 was varied by using 0.005 mg/suppository of naloxone hydrochloride.

EXAMPLE 18

The formulation of Example 16 was modified with 0.0067 mg/suppository of naltrexone hydrochloride substituted for the naloxone hydrochloride of Example 16.

EXAMPLE 19

The formulation of Example 16 was modified with 0.005 mg/suppository of naltrexone hydrochloride substituted for the naloxone hydrochloride of Example 16.

EXAMPLE 20

The formulation of Example 16 was modified with 0.0067 mg/suppository of nalmefene hydrochloride substituted for the naloxone hydrochloride of Example 16.

EXAMPLE 21

The formulation of Example 16 was modified with 0.005 mg/suppository of nalmefene hydrochloride substituted for the naloxone hydrochloride of Example 16.

We claim:

1. An analgesic composition in parenteral unit dosage form or in a unit dosage form suitable for delivery via the mucosa comprising an amount of buprenorphine which is less than the effective dose required to achieve pain relief and an amount of naloxone such that the ratio by weight of buprenorphine to naloxone is in the range of from 12.5:1 to 27.5:1, whereby the analgesic action of the buprenorphine is potentiated by the low dose of naloxone.

2. A composition as claimed in claim 1 wherein the unit dosage form contains an amount of naloxone such that the ratio by weight of buprenorphine to naloxone is in the range of from 15:1 to 20:1.

3. An analgesic composition as claimed in claim 1 in which buprenorphine is present in an amount of from 15 µg to 200 µg per unit dose.

4. A composition as claimed in claim 3 wherein the unit dosage form contains an amount of naloxone such that the ratio by weight of buprenorphine to naloxone is in the range of from 15:1 to 20:1.

5. An analgesic composition according to claim 3 which is in sublingual unit dosage form.

* * * * *